United States Patent [19]

Smith

[11] Patent Number: 5,149,457

[45] Date of Patent: Sep. 22, 1992

[54] STABLE MIXED LITHIUM AMIDE REAGENT COMPOSITIONS

[75] Inventor: W. Novis Smith, Philadelphia, Pa.

[73] Assignee: Cyprus Foote Mineral Company, Malvern, Pa.

[21] Appl. No.: 374,740

[22] Filed: Jun. 30, 1989

[51] Int. Cl.$^5$ ................................................ C09K 3/00
[52] U.S. Cl. ...................................................... 252/182.12
[58] Field of Search .................................... 252/182.12

[56] References Cited

U.S. PATENT DOCUMENTS

| | | | |
|---|---|---|---|
| 3,542,512 | 11/1970 | Honeycutt | 23/190 |
| 4,595,779 | 6/1986 | Morrison et al. | 564/2 |
| 4,622,410 | 11/1986 | Hamanaka et al. | 549/304 |
| 4,629,581 | 12/1986 | Boller et al. | 252/299.63 |
| 4,693,841 | 9/1987 | Hittich et al. | 252/299.62 |
| 4,827,007 | 5/1989 | Choi | 556/444 |
| 5,011,947 | 4/1991 | Catt et al. | 549/292 |

OTHER PUBLICATIONS

Schlosser et al., *Chem. Ber., 102*, 1944–53 (1969).
Normant et al., *Chem. Abs.*, 70, Abs #105864h (1969).
Stowell, *Carbonanions in & Organic Synthesis*, pp. 14–15, John Wiley & Sons (1979).
Lockmann et al., *J. Organometallic Chem.*, 179, 123–132 (1979).
Brochure "Lithium Diisopropylamide", Lithium Corp. of America, (CAS Reg. #4111-54-0) (1987).

*Primary Examiner*—Edward A. Miller
*Attorney, Agent, or Firm*—John Lezdey

[57] ABSTRACT

A method for preparing lithium amides in a monocyclic aromatic solvent and the reagent compositions formed thereby.

10 Claims, No Drawings

STABLE MIXED LITHIUM AMIDE REAGENT COMPOSITIONS

BACKGROUND OF THE INVENTION

The present invention relates to stable lithium amides and reagent compositions which are free of tetrahydrofuran and ethers. More particularly, the invention concerns the preparation of lithium amides and to reagent compositions thereof containing increased concentrations of the lithium amide in solution and capable of producing increased yields in subsequent reactions.

Lithium amides, for example, lithium diisopropopylamide are widely used as a reagents in the preparation of pharmaceuticals and specialty chemicals. Lithium amides are particularly useful for the preparation of lithium acetylide compounds which are used to form acetylenic substituted organic compounds such as steroid and fragrance intermediates. In order to form the lithium acetylide, acetylene is reacted with a lithium amide such as lithium diisopropylamide just prior to reacting the newly formed lithium acetylide with the ketone or other reagent in the same reactor. All of these steps are performed below 0° C. Usually, it is necessary to add an ether cosolvent such as tetrahydrofuran at this point to increase the limited solubility of the reagents and the subsequently formed lithium salt of the product from the reaction with the ketone. The lithium amide may be added as a preformed solution or it may be formed in the same reactor by reacting an alkyllithium such as n-butyllithium with an amine such as diisopropyl amine. In either case the lithium amide usually exhibits lower solubility than desired for maximum reactivity and yet there is a need to minimize the amount of solvents employed.

In order to increase the concentration of the lithium amide in the preformed solutions, ethers such as tetrahydrofuran and or complexing agents such as organomagnesium compounds have been added to increase the solubility of the lithium amide in solution. The presence of the ethers makes these solutions unstable and they decompose on standing in storage. The presence of magnesium compounds in the reaction and subsequent workup is undesirable because the possibility of lower reactivity and yields of desired products plus the more difficult workup due to the presence of the formed magnesium oxide which is highly insoluble and formed during washing.

Additionally when tetrahydrofuran is used as the solvent it has been found necessary to limit the amount of tetrahydrofuran to no more than one mole for each mole of lithium amide in order to minimize degradation of the system.

Aromatic solvents were not utilized as the solvent for preparing preformed lithium amide solutions in the past because the increased solubility was not appreciated and the belief that there would result a degradation of the alkyl lithium in an aromatic solution.

U.S. Pat. No. 4,595,779 to Morrison et al relates to a composition and method for preparing lithium diisopropylamide by the reaction of lithium metal and diisopropylamine in tetrahydrofuran and an inert liquid hydrocarbon cosolvent including styrene as an electron carrier. However, the use of tetrahydrofuran is considered essential in the preparation when utilizing lithium metal.

The article of Keith Smith entitled "Lithiation and Organic Synthesis", *Chemistry In Britain*, January 1982, pages 29-32, discloses the preparation lithium dialkyl amides for use as lithiating agents by the reaction of organolithium reagents in aliphatic hydrocarbon solvents.

U.S. Pat. No. 3,542,512 to Honeycutt relates to the preparation of lithium amide by contacting lithium metal with liquid ammonia and then heating the mixture at a temperature above 150 degrees C. in an inert liquid medium. The inert liquid medium includes aromatic compounds having a boiling point above 200 degrees C.

It is an object of the present invention to provide a lithium amide reagent composition having greater amounts of the lithium amide in solution.

It is a further object of the invention to provide a process for preparing lithium amides in higher concentrations in solution and in a solvent which is stable.

It is a yet further object of the invention to solubilize lithium amides which are considered insoluble.

It is a yet still further object of the invention to prepare lithium amides in situ and to utilize the resulting mixture to carry on further reactions.

It is still another object of the invention to prepare novel lithium amides and reagent compositions thereof.

SUMMARY OF THE INVENTION

In accordance with the present invention it has been found that alkyl lithiums could be reacted with amines in aromatic solvents to form lithium amide reagent compositions having greater amounts of reactive amides in solution. Moreover, the resulting lithium amide reagent compositions have more thermal stability than prior compositions.

The invention provides the preparation of lithium amides by the step of reacting an alkyl lithium and an amine of the formula selected from the group consisting of:

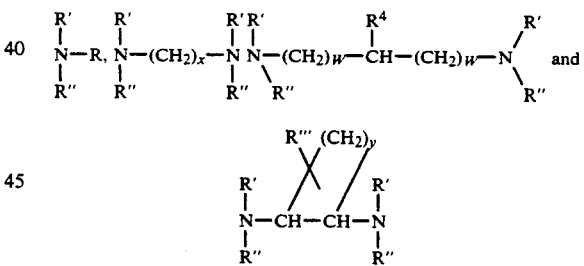

wherein R is an alkyl of 1 to 8 carbon atoms, alkyl phenyl or an alkyl monocyclic aliphatic group, R' and R" are the same or different and each represent hydrogen, an alkyl of 1 to 8 carbon atoms or an alkyl monocyclic aliphatic group, R''' is hydrogen, alkyl or alkoxy, $R^4$ is alkyl or phenyl; W is from 0 to 4, x is an integer of 2 to 8, and y is an integer of 2 to 6, with the proviso that at least one of R, R' and R" is hydrogen, in a monocyclic aromatic solvent.

The aromatic solvent which may be used in connection with the present invention include benzene, toluene, ethyl benzene, cumene, xylene, and the like. The amines which may be utilized in the preparation of the lithium amides of the invention include the alkyl amines such as methyl amine, isopropyl amine, isoamylamine and the like, dialkyl amines such as dimethyl amine, diethyl amine, diisopropyl amine, diisobutyl amine, diisoamyl amine, dialkyl heptyl amine, dialkylhexyl amine, for example, dimethyl hexylamine and diethyl hexyl amine, N, N'-dialkyl alkylene diamine, for example, N, N'-di(tert-butyl)ethylene diamine, N, N-dimethylaminoethyl amine, N, N-dimethyl aminopropyl amine, N, N, N'-trimethylethylene diamine, N, N-dipropylaminopropylene amine, N, N'-diethyl -1, 3-propanediamine, N, N, N'-trimethylethylene diamine, N, N, N'-triethylethylene diamine, N, N-dimethyl-N'-ethylethylene diamine and the like.

The preferred amines which may be utilized in the invention include butyl amine, diisoamyl amine, diisobutyl amine, di sec butylamine, diisopropyl amine and diethylhexylamine.

It has been surprisingly discovered that the preparation of a mixture of lithium amides increases the solubility of the amides in the aromatic solvent. Also, the preparation of an ordinarily insoluble lithium amide together with a soluble lithium amide results in the solubility of said otherwise less soluble lithium amide. The process of the invention is especially suited for reactions containing branch chained dialkyl amines. For example, the addition of about 20% diisopropyl amine and 80% diisobutylamine to a stoichiometric amount of butyl lithium in toluene results in at least a 1.5 molar solution of a soluble mixture of the resulting lithium alkyl amides.

The preparation of the lithium amides in the aromatic solvent is not affected by the presence of an aliphatic or monocyclic aliphatic solvent, for example, heptane.

However, it is preferable that at least 50% of the solvent for the preparation of the lithium amide comprise a monocyclic aromatic solvent.

In accordance with another embodiment of the invention, there is prepared a reagent composition comprising a lithium amide selected from the group consisting:

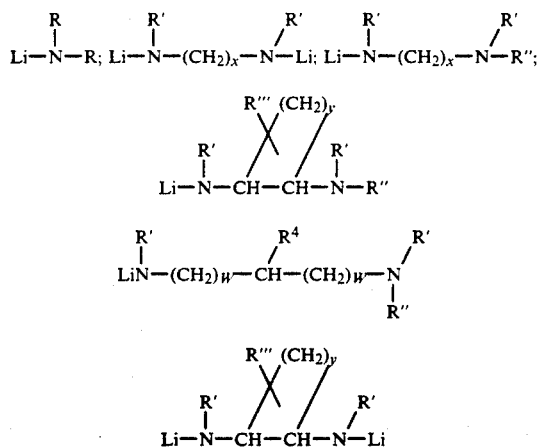

wherein R' and R" are the same or different and each represent hydrogen, an alkyl of 1 to 8 carbon atoms alkyl phenyl or an alkyl monocyclic aliphatic group, R'" is hydrogen, alkyl or alkoxy, R$^4$ is alkyl or phenyl, W is from 0 to 4, x is an integer of 2 to 8, and y is an integer of 2 to 6, and a monocyclic aromatic solvent.

Preferable of the lithium amides of the above formulas are those wherein at least one of R' is hydrogen. More preferable are those wherein R' is hydrogen on the same nitrogen atom with lithium.

The alkyl monocyclic aliphatic group includes methyl heptyl, ethyl heptyl, butyl heptyl, methyl hexyl, ethyl hexyl, butyl hexyl and the like.

If desired, the solvent may include a monocyclic aliphatic solvent such as pentane, heptane and hexane.

The lithium amide is generally found in at least a 0.5 molar concentration and in many cases in a concentration greater than 1.5M when prepared in situ in the aromatic solvent. The reagent composition of the invention can provide supersaturated solutions of lithium amides for use in various reactions, for example, the preparation of acetylides.

The concentration of the lithium amides in the reagent composition is increased by forming a solution containing a mixture of lithium amides. The reagent compositions of the invention include solutions containing at least 5% of ordinarily less soluble lithium amides which have been brought into solution in aromatic solvents by being prepared therein in situ.

The following examples are illustrative of the practice of the method of the present invention. It will be understood, however, that is not to be construed as in any way limitative of the full scope of the invention since various changes can be made, without departing from the spirit of the teachings contained herein, in the light of the guiding principles which have been set forth above. All percentages herein stated are based on weight except wherein noted.

EXAMPLE 1

Preparation of Mixed Lithium Amides

To 20 ml. of n-butyl lithium (0.04M) in toluene is added 4 ml. of diisobutylamine and 2.8 ml. of diisopropyl amine in toluene. The mixture is stirred for 10 minutes. A 22% by weight reagent composition is formed containing a 50-50 mole % by weight of mixed lithium amides.

EXAMPLE 2

Preparation of Lithium Diisopropyl Amide 8.4 ml. of diisopropyl amine was mixed with 29 ml. of butyl lithium in toluene (0.04M). The mixture became very viscous. 10 ml. of toluene was added and the mixture permitted to stand overnight. The mixture was hazy and without any precipitation.

EXAMPLE 3

Preparation of Lithium Diisobutylamide 4 ml. of diisobutyl amine was added to a 2.0M solution of n-butyl lithium in toluene. A clear solution was obtained of lithium diisobutylamide.

EXAMPLE 4

To demonstrate the increased solubility of the amides of the invention the following experiments were performed. Molar equivalents of the corresponding amines and diamines were added to 20 ml of 15% n-butyllithium in heptane and in toluene under nitrogen. The addition was carefully performed with syringes and the glass bottle was then capped after the reaction subsided, about 2 minutes. The solutions were permitted to stand two weeks at 20 degrees C. with intermittent shaking to be certain crystals had equilibrated with the solution. 2 ml samples were taken and filtered and then injected into 25 ml water and titrated with 0.1N HCl with adequate stirring. A pH meter was used to determine the end point of 7.0. There was no apparent break for the LiOH and the amine or diamine present. Therefore the total titration was divided by the equivalents of base present. For each mole of the amide formed, the titiation would be divided by two for monoamines and three for diamines. Table 1 lists the results:

TABLE 1

SOLUBILITIES OF VARIOUS LITHIUM AMIDES
Molar (weight %) @ 20 degrees C.

| AMINE REACTANT | TOLUENE | HEPTANE |
| --- | --- | --- |
| diisopropyl amine | 0.49 (5.29) | 0.42 (5.79) |
| diisobutyl amine | 1.44 (20.1) | 1.08 (5.79) |
| diisoamyl amine | 1.27 (21.8) | 0.92 (20.2) |
| dimethylaminopropyl amine | >1.6 | 1.04 (16.5) |
| diethylaminopropyl amine | 1.46 (22.9) | 1.07 (21.4) |
| dipropylaminopropyl amine | 1.31 (21.6) | 1.09 (23.1) |
| dimethylaminoethyl amine | 1.34 (14.5) | 1.01 (13.9) |
| diethylaminoethyl amine | 1.71 (21.2) | 1.04 (18.7) |
| N, N'-di-t-butylethylene diamine | 0.95 (19.5) | 0.66 (17.2) |
| N, N, N'-trimethylethylene diamine | 1.35 (16.7) | 1.01 (16.0) |
| N, N, N'-triethylethylene diamine | 1.18 (18.4) | 0.91 (18.1) |
| N, N, N'-trimethyl-1, 3-propylene diamine | >1.75 (24.6) | 1.28 (22.9) |

What is claimed is:

1. A reagent composition having improved thermal stability and which is free of ether consisting essentially of at least a 0.5 Molar concentration solution of a mixture of lithium amides selected from the group consisting of:

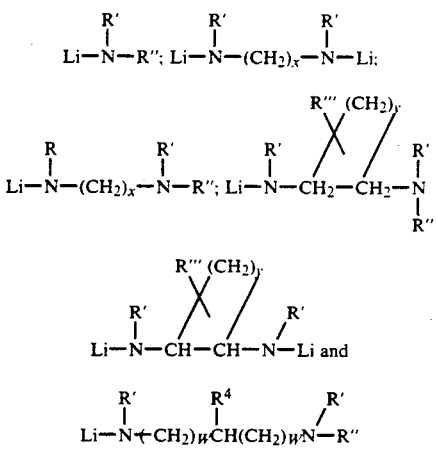

wherein

R, R' and R" are the same or different and each represent hydrogen, an alkyl of 1 to 8 carbon atoms or an alkyl monocyclic aliphatic group, R''' is hydrogen, alkyl or alkoxy, $R^4$ is alkyl or phenyl, W is from 0 to 4, x is an integer of 2 to 8, and y is an integer of 2 to 6, and a monocyclic aromatic solvent, said reagent composition being derived from the reaction of n-alkyl lithium and at least two amines.

2. The composition of claim 1 wherein said composition comprises a saturated solution of said lithium amides.

3. The composition of claim 1 wherein said composition comprises a supersaturated solution of said lithium amides.

4. The composition of claim 1 wherein said solvent is selected from the group consisting of benzene, toluene, ethyl benzene, cumene and xylene.

5. The composition of claim 1 comprising lithium diisopropyl amide.

6. The composition of claim 1 comprising lithium diisobutyl amide.

7. A reagent composition comprising a mixture of lithium diisobutyl amide and lithium diisopropyl amide in a monocyclic aromatic solvent, said composition comprising at least a 0.5 molar concentration of said amides in solution.

8. An ether-free reagent composition having improved thermal stability consisting essentially of at least a 0.5 molar concentration solution of a mixture of lithium amides of the formula consisting of

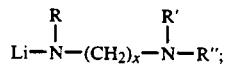

wherein R, $R^1$ and R" are the same or different and each represent hydrogen, an alkyl group of 1 to 8 carbon atoms or an alkyl monocyclic aliphatic group, and x is an integer of 2 to 8, in a monocyclic aromatic solvent, said lithium amides being the reaction product of n-alkyl lithium and a mixture of diamines.

9. The reagent composition of claim 8 wherein said diamines are diisopropyl amine and diisobutylamine and said alkyl lithium is N-butyl lithium.

10. The reagent composition of claim 8 wherein said solvent comprises toluene.

* * * * *